United States Patent [19]

Kawai et al.

[11] Patent Number: 4,835,291

[45] Date of Patent: May 30, 1989

[54] DIVINYL COMPOUNDS AND CHROMOGENIC RECORDING-MATERIAL PREPARED BY USING THEREOF

[75] Inventors: Hajime Kawai; Yoshiharu Fujino, both of Tsuzuki; Youji Shimizu, Kyoto; Seiichi Nieda, Kyoto; Kazuhiko Gendai, Kyoto; Katsuhiko Tsunemitsu, Kyoto, all of Japan

[73] Assignee: Yamada Chemical Co., Ltd., Kyoto, Japan

[21] Appl. No.: 37,665

[22] Filed: Apr. 13, 1987

[30] Foreign Application Priority Data

Apr. 16, 1986 [JP] Japan .................................. 61-88961
May 1, 1986 [JP] Japan ................................ 61-102909
Feb. 2, 1987 [JP] Japan .................................. 62-23361

[51] Int. Cl.⁴ ..................... C07D 307/88; B41M 5/16; B41M 5/18; B41M 5/22
[52] U.S. Cl. .................................. 549/304; 503/220; 503/223; 427/151
[58] Field of Search ......................... 549/304; 503/220

[56] References Cited

FOREIGN PATENT DOCUMENTS 0062544 10/1982 European Pat. Off. ............ 503/220
0127203 12/1984 European Pat. Off. ............ 503/220
0188377  7/1986 European Pat. Off. ............ 503/220
2218895 11/1972 Fed. Rep. of Germany ...... 549/304
 608364  6/1983 Japan ................................. 503/220

OTHER PUBLICATIONS

Chemical Abstracts, vol. 102, No. 22, Jun. 3, 1985, p. 684, Abstract No. 195296f.

Chemical Abstracts, vol. 107, No. 6, Aug. 10, 1987, p. 663, Abstract No. 49640a.
European Search Report.

Primary Examiner—Mary C. Lee
Assistant Examiner—J. Richter
Attorney, Agent, or Firm—Nixon & Vanderhye

[57] ABSTRACT

Disclosed herein are novel divinyl compounds represented by the formula (I):

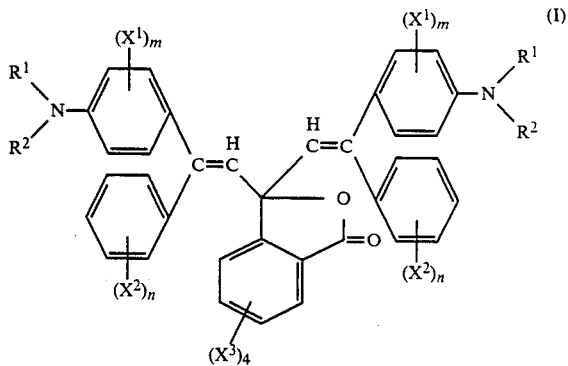

and a recording-material prepared by utilizing the divinyl compounds.

The divinyl compound is in itself almost colorless, extremely stable in the atmosphere and develops rapidly blackish color by a developer. The color image given by the divinyl compound is excellent in light-resistance and moisture-resistance and the letters developed can be read by an optical letter-reading apparatus or a barcord reading apparatus.

37 Claims, 3 Drawing Sheets

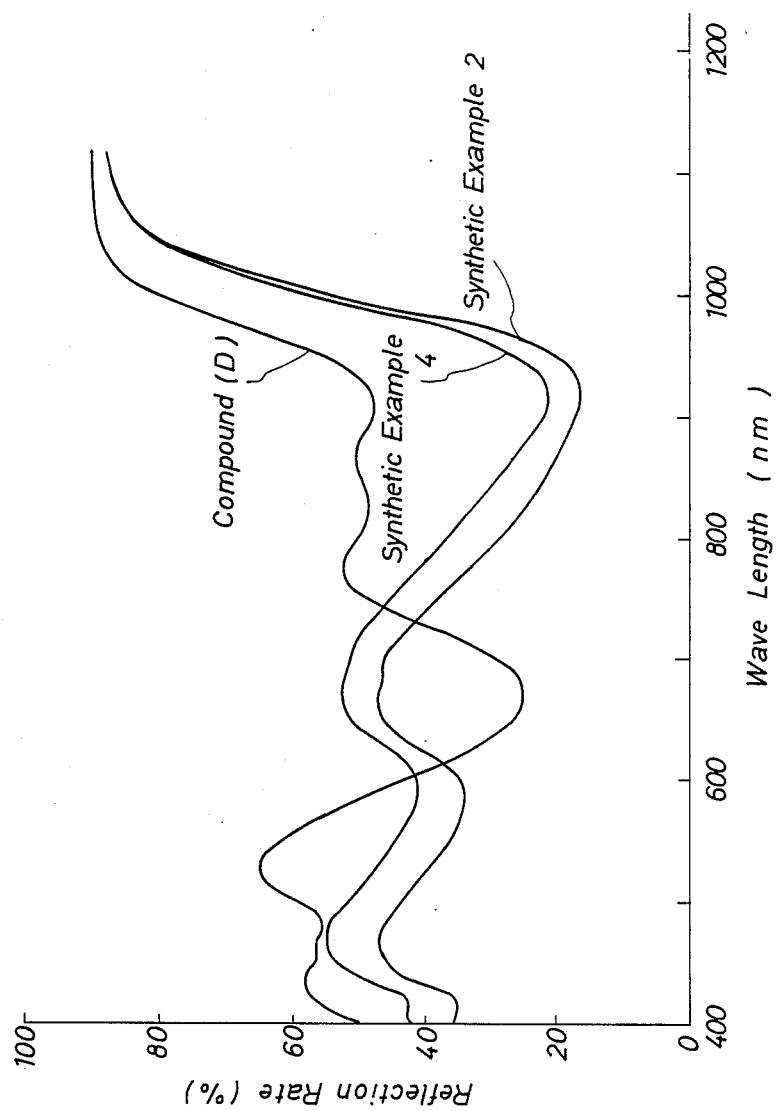

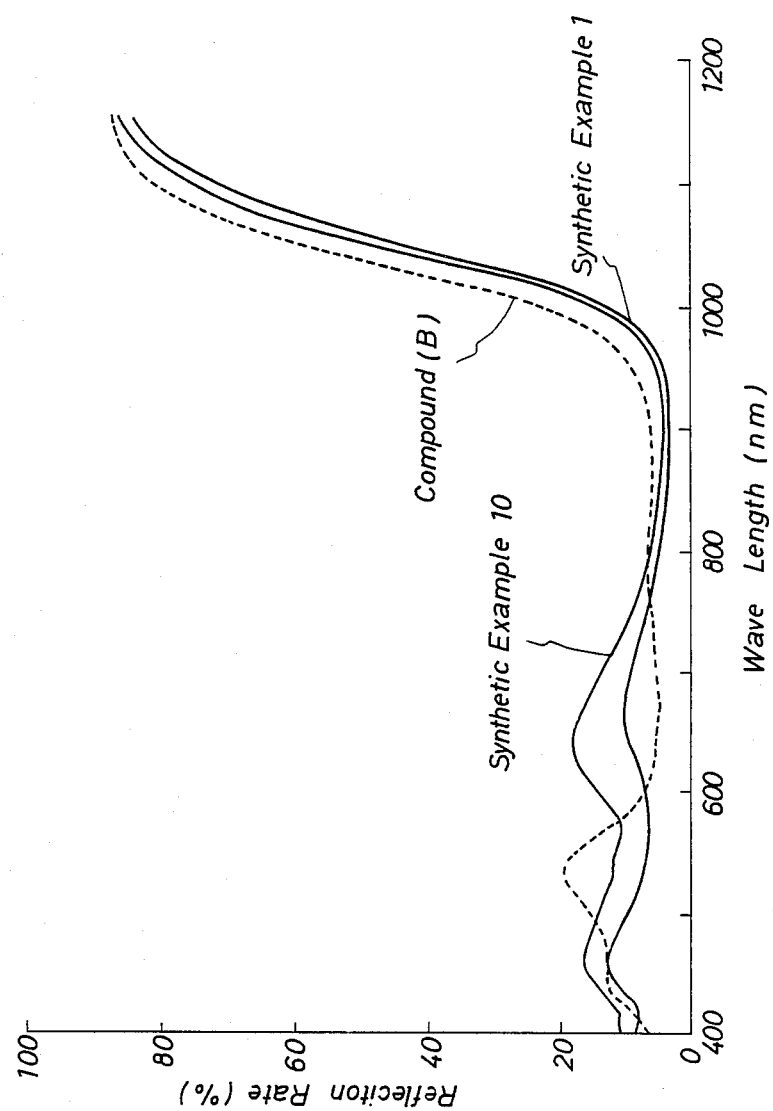

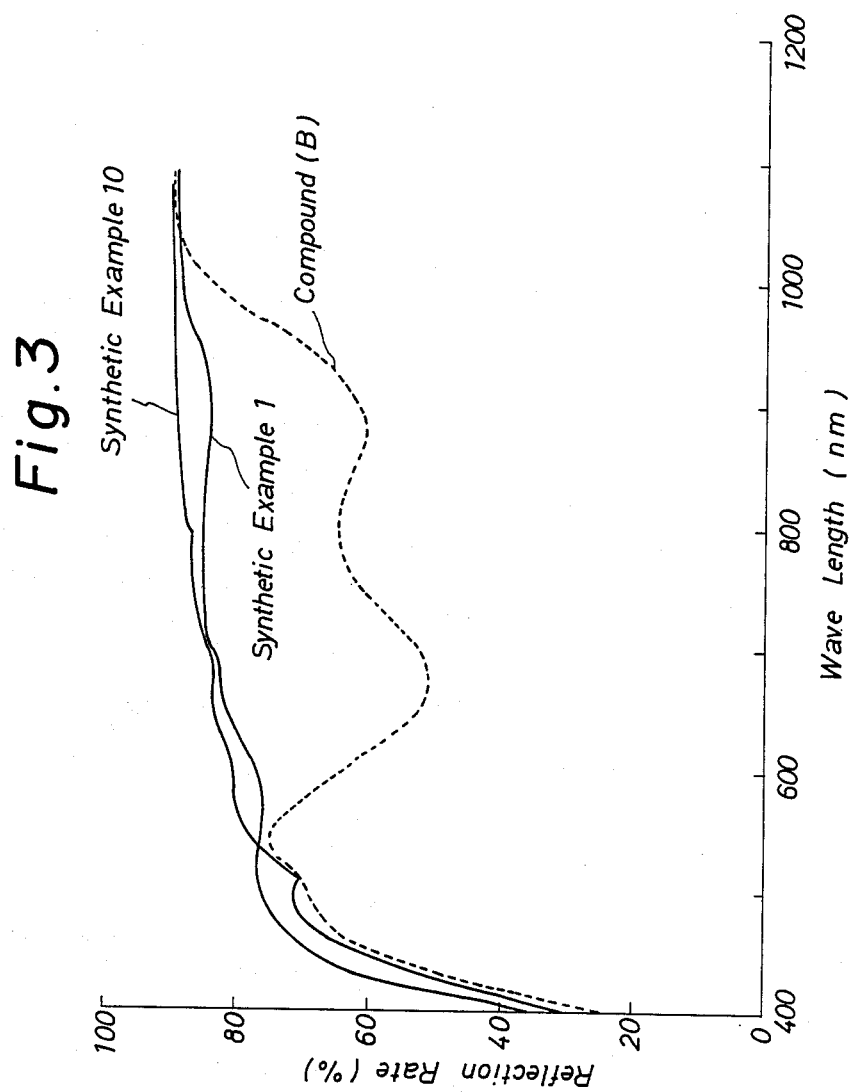

DIVINYL COMPOUNDS AND CHROMOGENIC RECORDING-MATERIAL PREPARED BY USING THEREOF

BACKGROUND OF THE INVENTION:

The present invention relates to a recording-material such as pressure-sensitive recording paper, heat-sensitive recording paper, electro-heat sensitive recording paper, etc. More in detail, the present invention relates to a recording-material prepared by using a divinyl phthalide compound represented by the formula (I):

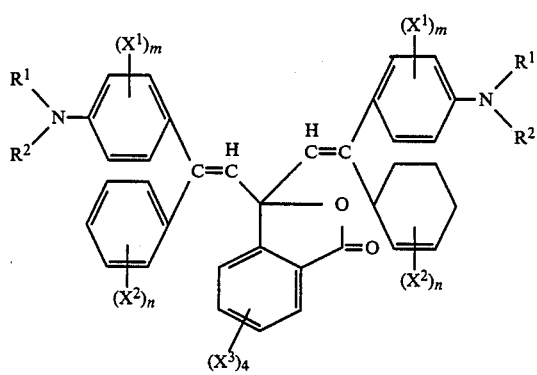

wherein $X^1$ represents an alkyl group, an alkoxy group or a halogen atom; $X^2$ represents an alkyl group, an alkoxy group, a halogen atom or a group of $R^3O—$; $X^3$ represents a halogen atom; $R^1$ represents a hydrogen atom, an alkyl group, an alkoxyalkyl group, a haloalkyl group, an alkyenyl group, an aralkyl group, a cyclohexylmethyl group, a methylcyclohexyl group, a trimethylcyclohexyl group, a furfuryl group, a tetrahydrofuryl group or a tetrahydropyrane-2-yl-methyl group; $R^2$ represents a cycloalkyl group, a phenyl group or a benzyl group having chlorine atom(s), bromine atom(s) or alkyl group(s) of not more than 4 carbon atoms as the substituent, or optional group $R^1$; $R^3$ represents a cycloalkyl group, an alkoxyalkyl group, an alkenyl group, a haloalkyl group, an aralkyl group or an aryl group; and m and n represent an integer of 0, 1, 2 or 3, respectively. When m and n are not less than 2, $X^1$ of $(X^1)_m$, $X^2$ of $(X^2)_n$ or $X^3$ of $(X^3)_4$ can be same or different. (Hereinafter the same sign means the same meaning).

The divinyl phthalide compounds represented by the formula (I) are the novel compounds synthesized for the first time by the present inventors. The compounds are by themselves almost colorless, extremely stable in the atmosphere, have no subliming property and spontaneously chlomogenic property and dissolve extremely well in organic solvents. They give a blackish color rapidly by a developer and its color image is excellent in light-resistance and moisture-resistance. Furthermore, since the color image has a strong absorption between 700 and 1000 nm in addition of the visible region, the color image has a distinctive feature that it is possible to be read by the optical letter-reading apparatus using the near infrared rays (such as OCR and OMR) and the barcord reading apparatus. Namely, the divinyl phthalide compound of the present invention (hereinafter referred to as the present compound) is an extremely valuable and novel compound which can be used as a chromogenic agent for an ordinary recording-material developing black color, of which demand is rapidly increasing recently, as well as the material readable with OCR, OMR, etc.

The color image due to the black-coloring fluoran compound (A), which has been used as a conventional chromogenic agent for a recording-material, does not have any absorption in the near infrared region and accordingly, the color image could not be read by an optical letter-reading apparatus (refer to FIG. 2):

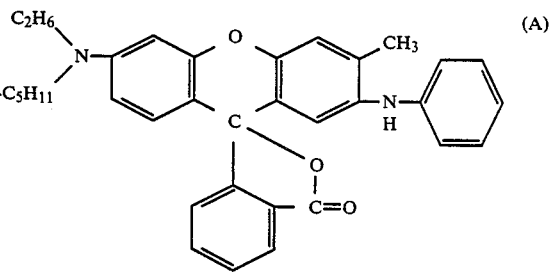

(refer to Japanese Patent Publication No. 56-52759/1981).

On the other hand, as the chromogenic agents having an absorption in the near infrared region, some compounds have been recently proposed in Japanese Patent Publication No. 58-5940/1983, Japanese Patent Application Laid-Open (KOKAI) No. 59-199757/1984 and Japanese Patent Application Laid-Open (KOKAI) No. 60-230890/1985. However, each of the proposed compounds has the following defects and any satisfactory chromogenic agent has not been obtained in the present situation.

Namely, the compound (B) of Japanese Patent Publication No. 58-5940/1983 and the compound (C) of Japanese Patent Application Laid-Open (KOKAI) No. 60-230890/1985 have been themselves strongly colored in yellow and besides, they are strong in the spontaneous coloring. These defects have very had effect on production of the recording materials.

Although the fluorene compound (D) of Japanese Patent Application Laid-Open (KOKAI) No. 59-199757/1984 is colorless, the chromogenic property and the stability of color image are poor.

Furthermore, the hue of each of compounds (B), (C) and (D), when developed color, is green and accordingly, to obtain blackish color, another chromogenic agent giving red or black color must be added in a large amount, and since the chromogenic property and the chromogenic speed of each agent are different from those of compounds (B), (C) and (D) and particularly, the light-resistance of red-chromogenic agent is generally poor, bad influences such as unbalance of color-development and reduction of light-resistance could not be avoided.

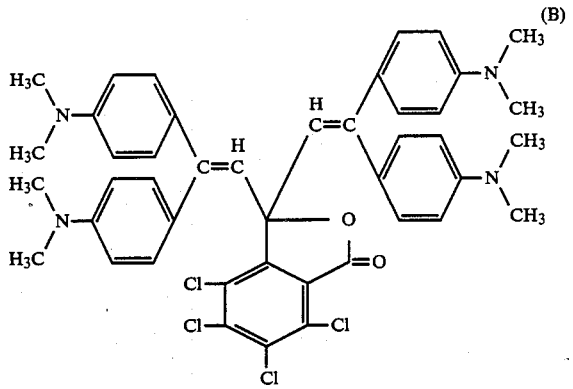

(refer to Japanese Patent Publication No. 58-5940/1983).

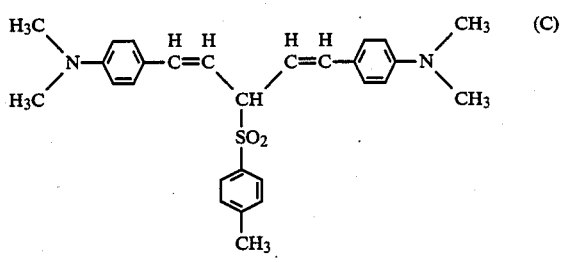

(refer to Japanese Patent Application Laid-Open (KOKAI) No. 60-230890/1985).

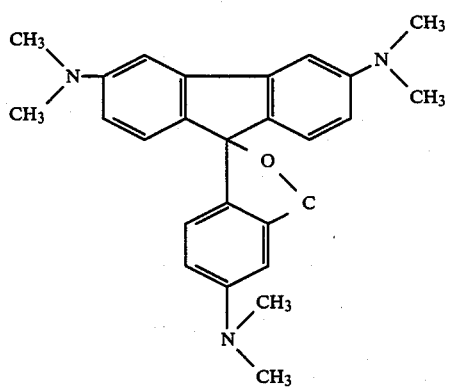

(refer to Japanese Patent Application Laid-Open (KOKAI) No. 59-199757/1984).

As a result of the present inventors earnest studies to improve the defects of the conventional chromogenic agents, the present invention has been attained.

The present invention has been attained by the present inventors who have found out that the divinyl compounds (I) are unexpectedly excellent in several properties such as the solubility, the coloring of the compound itself, the hue of the developed color, the chromogenic property, the absorbancy of near infrared rays and the stability of color image and have studied further the problems, and the present invention provides the compounds represented by the formula (I) and a chromogenic recording materials, which contains the compound (I) as a chromogenic agent.

SUMMARY OF THE INVENTION:

The object of the present invention lies in offering a novel divinyl compound represented by the following formula (I):

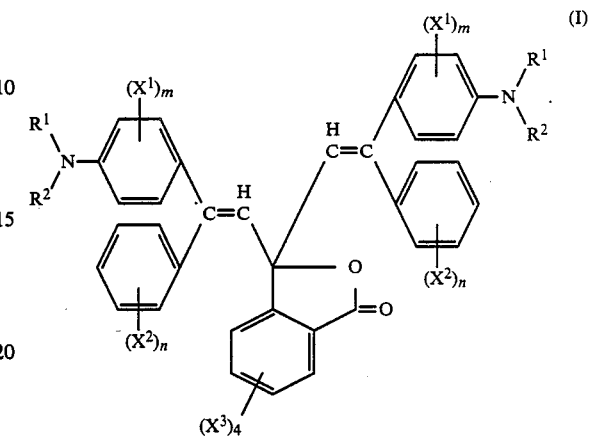

Furthermore, the object of the present invention lies in offering a chromogenic dye-precursor material of blackish color represented by the formula (I).

Still more, the object of the present invention lies in offering a recording-material comprising a material containing the divinyl compound represented by the formula (I) as a chromogenic agent.

BRIEF EXPLANATION OF THE DRAWINGS:

Of the attached drawings, FIGS. 1 and 2 are the reflection spectra of a color image of pressure-sensitive and heat-sensitive recording paper prepared with the present compound and the referenced compound, respectively, and FIG. 3 is the reflection spectra of a texture of heat-sensitive recording paper prepared with the present compound and the referenced compound.

DETAILED DESCRIPTION OF THE INVENTION:

The present compound is a divinyl compound represented by the following formula (I):

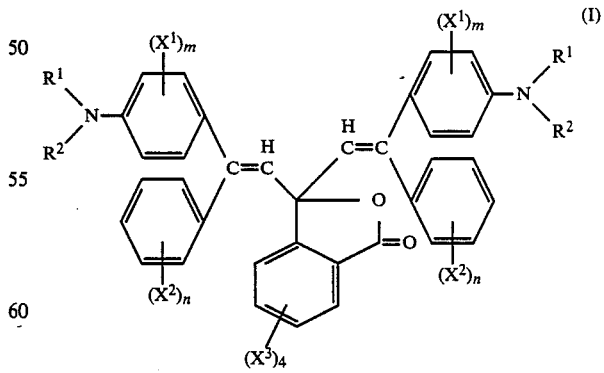

and as the concrete example thereof, the following compounds may be exemplified. Every compound is an almost colorless or pale yellow solid and develops a blue-black to black color rapidly by the action of activated clay.

1. 3,3-Bis[2-(p-dimethylaminophenyl)-2-(p-methoxyphenyl)-ethenyl]-4,5,6,7-tetrachlorophthalide
2. 3,3-Bis[2-(p-dimethylaminophenyl)-2-(p-ethoxyphenyl)-ethenyl]-4,5,6,7-tetrachlorophthalide
3. 3,3-Bis[2-(p-diethylaminophenyl)-2-(p-methoxyphenyl)-ethenyl]-4,5,6,7-tetrachlorophthalide
4. 3,3-Bis[2-(p-dimethylaminophenyl)-2-(p-propoxyphenyl)-ethenyl]-4,5,6,7-tetrachlorophthalide
5. 3,3-Bis[2-(p-dimethylaminophenyl)-2-(p-isopropoxyphenyl)-ethenyl]-4,5,6,7-tetrachlorophthalide
6. 3,3-Bis[2-(p-dimethylaminophenyl)-2-(p-butoxyphenyl)-ethenyl]-4,5,6,7-tetrachlorophthalide
7. 3,3-Bis[2-(p-dimethylaminophenyl)-2-(p-isobutoxyphenyl)-ethenyl]-4,5,6,7-tetrachlorophthalide
8. 3,3-Bis[2-(p-methylethylaminophenyl)-2-(p-methoxyphenyl)-ethenyl]-4,5,6,7-tetrachlorophthalide
9. 3,3-Bis[2-(p-methylpropylaminophenyl)-2-(p-methoxyphenyl)-ethenyl]-4,5,6,7-tetrachlorophthalide
10. 3,3-Bis[2-(p-dimethylaminophenyl)-2-(p-methylphenyl)-ethenyl]-4,5,6,7-tetrachlorophthalide
11. 3,3-Bis[2-(p-ethylpropylaminophenyl)-2-(p-methoxyphenyl)-ethenyl]-4,5,6,7-tetrachlorophthalide
12. 3,3-Bis[2-(p-methylisopropylaminophenyl)-2-(p-methoxyphenyl)ethenyl]-4,5,6,7-tetrachlorophthalide
13. 3,3-Bis[2-(p-ethylisopropylaminophenyl)-2-(p-methoxyphenyl)ethenyl]-4,5,6,7-tetrachlorophthalide
14. 3,3-Bis[2-(p-dipropylaminophenyl)-2-(p-methoxyphenyl)-ethenyl]-4,5,6,7-tetrachlorophthalide
15. 3,3-Bis[2-(p-methylbutylaminophenyl)-2-(p-methoxyphenyl)ethenyl]-4,5,6,7-tetrachlorophthalide
16. 3,3-Bis[2-(p-ethylbutylaminophenyl)-2-(p-methoxyphenyl)-ethenyl]-4,5,6,7-tetrachlorophthalide
17. 3,3-Bis[2-(p-diethylaminophenyl)-2-(p-ethoxyphenyl)-ethenyl]-4,5,6,7-tetrachlorophthalide
18. 3,3-Bis[2-(p-dimethylaminophenyl)-2-(m-methyl-p-methoxyphenyl)ethenyl]-4,5,6,7-tetrachlorophthalide
19. 3,3-Bis[2-(p-dimethylaminophenyl)-2-(p-pentyloxyphenyl)-ethenyl]-4,5,6,7-tetrachlorophthalide
20. 3,3-Bis[2-(p-dimethylaminophenyl)-2-(p-methoxyphenyl)-ethenyl]-4,5,6,7-tetrabromophthalide
21. 3,3-Bis[2-(p-dimethylaminophenyl)-2-(p-isopentyloxyphenyl)ethenyl]-4,5,6,7-tetrachlorophthalide
22. 3,3-Bis[2-(p-dimethylaminophenyl)-2-(m,p-dimethoxyphenyl)ethenyl]-4,5,6,7-tetrachlorophthalide
23. 3,3-Bis[2-(p-methylpropylaminophenyl)-2-(p-ethoxyphenyl)-ethenyl]-4,5,6,7-tetrachlorophthalide
24. 3,3-Bis[2-(p-ethylpropylaminophenyl)-2-(p-ethoxyphenyl)-ethenyl]-4,5,6,7-tetrachlorophthalide
25. 3,3-Bis[2-(p-dimethylaminophenyl)-2-(p-ethylphenyl)-ethenyl]-4,5,6,7-tetrachlorophthalide
26. 3,3-Bis[2-(p-dimethylaminophenyl)-2-phenylethenyl]-4,5,6,7-tetrachlorophthalide
27. 3,3-Bis[2-(p-dimethylaminophenyl)-2-(p-tert-butoxyphenyl)-ethenyl]-4,5,6,7-tetrachlorophthalide
28. 3,3-Bis[2-(p-dimethylaminophenyl)-2-(p-sec-butoxyphenyl)-ethenyl]-4,5,6,7-tetrachlorophthalide
29. 3,3-Bis[2-(p-dimethylcyclohexylaminophenyl)-2-(p-methoxyphenyl)ethenyl]-4,5,6,7-tetrachlorophthalide
30. 3,3-Bis[2-(p-dimethylaminophenyl)-2-(p-methoxyphenyl)-ethenyl]-5,6-dichloro-4,7-dibromophthalide
31. 3,3-Bis[2-(p-dimethylaminophenyl)-2-(m,p-dimethylphenyl)-ethenyl]-4,5,6,7-tetrachlorophthalide
32. 3,3-Bis[2-(p-dimethylaminophenyl)-2-(o-methyl-p-methoxyphenyl)ethenyl]-4,5,6,7-tetrachlorophthalide
33. 3,3-Bis[2-(p-dimethylamino-o-methylphenyl)-2-phenylethenyl]-4,5,6,7-tetrachlorophthalide
34. 3,3-Bis[2-(p-dimethylamino-o-chlorophenyl)-2-(p-methylphenyl)ethenyl]-4,5,6,7-tetrachlorophthalide
35. 3,3-Bis[2-(p-dimethylamino-m-methylphenyl)-2-(p-methoxyphenyl)ethenyl]-4,5,6,7-tetrachlorophthalide
36. 3,3-Bis[2-(p-dimethylamino-o-ethylphenyl)-2-(p-methoxyphenyl)ethenyl]-4,5,6,7-tetrachlorophthalide
37. 3,3-Bis[2-(p-dimethylaminophenyl)-2-(p-chlorophenyl)-ethenyl]-4,5,6,7-tetrachlorophthalide
38. 3,3-Bis[2-(p-dimethylaminophenyl)-2-(o,p-dimethoxyphenyl)-ethenyl]-4,5,6,7-tetrachlorophthalide
39. 3,3-Bis[2-(p-dimethylaminophenyl)-2-(m-methoxyphenyl)-ethenyl]-4,5,6,7-tetrachlorophthalide
40. 3,3-Bis[2-(p-dipropylaminophenyl)-2-(p-methylphenyl)-ethenyl]-4,5,6,7-tetrachlorophthalide
41. 3,3-Bis[2-(p-dibutylamino-o-methylphenyl)-2-(p-methoxyphenyl)ethenyl]-4,5,6,7-tetrachlorophthalide
42. 3,3-Bis[2-(p-dihexylaminophenyl)-2-phenylethenyl]-4,5,6,7-tetrachlorophthalide
43. 3,3-Bis[2-(p-dimethylaminophenyl)-2-(p-octylphenyl)-ethenyl]-4,5,6,7-tetrachlorophthalide
44. 3,3-Bis[2-(p-dimethylaminophenyl)-2-(p-hexyloxyphenyl)-ethenyl]-4,5,6,7-tetrachlorophthalide
45. 3,3-Bis[2-(p-methylcyclohexylaminophenyl)-2-(p-methylphenyl)ethenyl]-4,5,6,7-tetrachlorophthalide
46. 3,3-Bis[2-(p-ethylbenzylaminophenyl)-2-(p-methoxyphenyl)-ethenyl]-4,5,6,7-tetrachlorophthalide
47. 3,3-Bis[2-(p-ethyltolylaminophenyl)-2-phenylethenyl]-4,5,6,7-tetrachlorophthalide
48. 3,3-Bis[2-(p-dimethylaminophenyl)-2-phenylethenyl]-4,5,6,7-tetrabromophthalide
49. 3,3-Bis[2-(p-dimethylaminophenyl)-2-(p-fluorophenyl)-ethenyl]-4,5,6,7-tetrabromophthalide
50. 3,3-Bis[2-(p-dimethylaminophenyl)-2-(p-chlorophenyl)-ethenyl]-4,5,6,7-tetrabromophthalide
51. 3,3-Bis[2-(p-dimethylaminophenyl)-2-(m,p-dimethoxyphenyl)ethenyl]-4,5,6,7-tetrabromophthalide
52. 3,3-Bis[2-(p-dimethylaminophenyl)-2-(m,p-dimethylphenyl)ethenyl]-4,5,6,7-tetrabromophthalide
53. 3,3-Bis[2-(p-dimethylaminophenyl)-2-phenylethenyl]-5-chloro-4,6,7-tribromophthalide
54. 3,3-Bis[2-(p-dimethylaminophenyl)-2-(m-methylphenyl)-ethenyl]-5-chloro-4,6,7-tribromophthalide
55. 3,3-Bis[2-(p-dimethylaminophenyl)-2-(p-hexyloxyphenyl)-ethenyl]-5-chloro-4,6,7-tribromophthalide
56. 3,3-Bis[2-(p-dimethylaminophenyl)-2-phenylethenyl]-6-chloro-4,5,7-tribromophthalide
57. 3,3-Bis[2-(p-dimethylamino-o-chlorophenyl)-2-(p-methylphenyl)ethenyl]-6-chloro-4,5,7-tribromophthalide
58. 3,3-Bis[2-(p-dimethylaminophenyl)-2-(p-methoxyphenyl)-ethenyl]-6-chloro-4,5,7-tribromophthalide
59. 3,3-Bis[2-(p-dimethylaminophenyl)-2-phenylethenyl]-5,6-dichloro-4,7-dibromophthalide
60. 3,3-Bis[2-(p-dimethylaminophenyl)-2-(m-methyl-p-methoxyphenyl)ethenyl]-5,6-dichloro-4,7-dibromophthalide
61. 3,3-Bis[2-(p-dimethylaminophenyl)-2-(m-methoxyphenyl)-ethenyl]-5,6-dichloro-4,7-dibromophthalide
62. 3,3-Bis[2-(p-dimethylaminophenyl)-2-(p-butoxyphenyl)-ethenyl]-4,5,6,7-tetrabromophenylphthalide
63. 3,3-Bis[2-(p-dimethylaminophenyl)-2-(p-hexyloxyphenyl)-ethenyl]-4,5,6,7-tetrabromophthalide
64. 3,3-Bis[2-(p-dimethylamino-o-methylphenyl)-2-(p-methylphenyl)ethenyl]-4,5,6,7-tetrabromophthalide
65. 3,3-Bis[2-(p-dimethylamino-m-methylphenyl)-2-(p-methoxyphenyl)ethenyl]-4,5,6,7-tetrabromophthalide
66. 3,3-Bis[2-(p-dimethylamino-m-ethoxyphenyl)-2-phenylethenyl]-4,5,6,7-tetrabromophthalide 67. 3,3-Bis[2-(p-diethylaminophenyl)-2-(p-methylphenyl)-ethenyl]-4,5,6,7-tetrabromophthalide
68. 3,3-Bis[2-(p-dipropylaminophenyl)-2-(p-methoxyphenyl)-ethenyl]-4,5,6,7-tetrabromophthalide
69. 3,3-Bis[2-(p-dibutylaminophenyl)-2-(p-methylphenyl)-ethenyl]-4,5,6,7-tetrabromophthalide
70. 3,3-Bis[2-(p-dihexylaminophenyl)-2-(p-methylphenyl)-ethenyl]-4,5,6,7-tetrabromophthalide
71. 3,3-Bis[2-(p-methylbutylaminophenyl)-2-(p-methylphenyl)-ethenyl]-4,5,6,7-tetrabromophthalide
72. 3,3-Bis[2-(p-methylcyclohexylaminophenyl)-2-(p-methoxyphenyl)ethenyl]-4,5,6,7-tetrabromophthalide
73. 3,3-Bis[2-(p-ethylbenzylaminophenyl)-2-phenylethenyl]-4,5,6,7-tetrabromophthalide
74. 3,3-Bis[2-(p-ethyltolylaminophenyl)-2-(p-methoxyphenyl)-ethenyl]-4,5,6,7-tetrabromophthalide
75. 3,3-Bis[2-(p-aminophenyl)-2-(p-methoxyphenyl)ethenyl]-4,5,6,7-tetrachlorophthalide
76. 3,3-Bis[2-(p-ethylaminophenyl)-2-(p-methoxyphenyl)-ethenyl]-4,5,6,7-tetrachlorophthalide
77. 3,3-Bis[2-(p-methylmethoxyethylaminophenyl)-2-(p-methoxyphenyl)ethenyl]-4,5,6,7-tetrachlorophthalide
78. 3,3-Bis[2-(p-methylethoxypropylaminophenyl)-2-(p-methoxyphenyl)ethenyl]-4,5,6,7-tetrachlorophthalide
79. 3,3-Bis[2-(p-dimethoxyethylaminophenyl)-2-(p-methylphenyl)ethenyl]-5-chloro-4,6,7-tribromophthalide
80. 3,3-Bis[2-(p-benzylmethoxypropylaminophenyl)-2-(p-ethoxyphenyl)ethenyl]-4,5,6,7-tetrachlorophthalide
81. 3,3-Bis[2-(p-cyclohexylethoxyethylaminophenyl)-2-phenylethenyl]-5,6-dichloro-4,7-dibromophthalide
82. 3,3-Bis[2-(p-methylmethoxyethylaminophenyl)-2-(p-chlorophenyl)ethenyl]-4,5,6,7-tetrachlorophthalide
83. 3,3-Bis[2-(p-ethylmethoxyethylamino-m-methylphenyl)-2-(p-methoxyphenyl)ethenyl]-4,5,6,7-tetrachlorophthalide
84. 3,3-Bis[2-(p-methylethoxypropylamino-m-ethoxyphenyl)-2-(p-methoxyphenyl)ethenyl]-4,5,6,7-tetrachlorophthalide
85. 3,3-Bis[2-(p-methylallylaminophenyl)-2-(p-methylphenyl)-ethenyl]-4,5,6,7-tetrachlorophthalide
86. 3,3-Bis[2-(p-diallylaminophenyl)-2-(p-methoxyphenyl)-ethenyl]-4,5,6,7-tetrachlorophthalide
87. 3,3-Bis[2-(p-ethyl-γ-chloropropylaminophenyl)-2-(m,p-dimethoxyphenyl)ethenyl]-4,5,6,7-tetrachlorophthalide
88. 3,3-Bis[2-(p-di-γ-chloropropylaminophenyl)-2-(p-ethoxyphenyl)ethenyl]-4,5,6,7-tetrabromophthalide
89. 3,3-Bis[2-(p-cyclopentyl-γ-chloropropylaminophenyl)-2-(p-butoxyphenyl)ethenyl]-4,5,6,7-tetrachlorophthalide
90. 3,3-Bis[2-(p-methylcyclohexylmethylaminophenyl)-2-(p-methoxy-m-methylphenyl)ethenyl]-4,5,6,7-tetrachlorophthalide
91. 3,3-Bis[2-(p-ethyl-4-methylcyclohexylaminophenyl)-2-phenylethenyl]-4,5,6,7-tetrafluorophthalide
92. 3,3-Bis[2-(p-methyl-3,3,5-trimethylcyclohexylaminophenyl)-2-(p-butylphenyl)ethenyl]-4,5,6,7-tetrachlorophthalide
93. 3,3-Bis[2-(p-4-methylbenzylmethoxypropylaminophenyl)-2-(m,p-dimethoxyphenyl)ethenyl]-4,5,6,7-tetrachlorophthalide
94. 3,3-Bis[2-(p-ethylfurfurylaminophenyl)-2-(m,p-dimethylphenyl)ethenyl]-4,5,6,7-tetrachlorophthalide
95. 3,3-Bis[2-(p-methyltetrahydrofurfurylaminophenyl)-2-(p-methoxyphenyl)ethenyl]-4,5,6,7-tetrachlorophthalide
96. 3,3-Bis[2-(p-ditetrahydrofurfurylaminophenyl)-2-(m-methyl-p-methoxyphenyl)ethenyl]-4,5,6,7-tetrachlorophthalide
97. 3,3-Bis[2-(p-benzyltetrahydrofurfurylaminophenyl)-2-(p-methoxyphenyl)ethenyl]-5-chloro-4,6,7-tribromophthalide
98. 3,3-Bis[2-(p-methyltetrahydropyrane-2-ylmethylaminophenyl)-2-(p-methoxyphenyl)ethenyl]-4,5,6,7-tetrachlorophthalide
99. 3,3-Bis[2-(p-methylmethoxyethylaminophenyl)-2-(p-methoxyphenyl)ethenyl]-4,5,6,7-tetrafluorophthalide
100. 3,3-Bis[2-(p-methylethoxypropylaminophenyl)-2-(p-methoxyphenyl)ethenyl]-4,5,6,7-tetrafluorophthalide
101. 3,3-Bis[2-(p-dimethoxyethylaminophenyl)-2-(p-methylphenyl)ethenyl]-5-chloro-4,6,7-triiodophthalide
102. 3,3-Bis[2-(p-dimethylaminophenyl)-2-(p-methoxyethoxyphenyl)ethenyl]-4,5,6,7-tetrachlorophthalide
103. 3,3-Bis[2-(p-dimethylaminophenyl)-2-(p-allyloxyphenyl)-ethenyl]-4,5,6,7-tetrachlorophthalide
104. 3,3-Bis[2-(p-dimethylaminophenyl)-2-(p-chloropropyloxyphenyl)ethenyl]-4,5,6,7-tetrachlorophthalide
105. 3,3-Bis[2-(p-dimethylaminophenyl)-2-(p-cyclolpentyloxyphenyl)ethenyl]-4,5,6,7-tetrachlorophthalide
106. 3,3-Bis[2-(p-dimethylaminophenyl)-2-(p-cyclohexyloxyphenyl)ethenyl]-4,5,6,7-tetrachlorophthalide
107. 3,3-Bis[2-(p-dimethylaminophenyl)-2-(p-benzyloxyphenyl)-ethenyl]-4,5,6,7-tetrachlorophthalide
108. 3,3-Bis[2-(p-dimethylaminophenyl)-2-(p-phenoxyphenyl)-ethenyl]-4,5,6,7-tetrachlorophthalide
109. 3,3-Bis{2-[p-dimethylaminophenyl]-2-[p-methoxyphenoxy)-phenyl]ethenyl}-4,5,6,7-tetrachlorophthalide
110. 3,3-Bis{2-[p-diethylaminophenyl]-2-[p-methoxyphenoxy)-phenyl]ethenyl}-4,5,6,7-tetrachlorophthalide The divinylphthalide compounds according to the present invention can be synthesized by the method shown below.

As a first step, an ethylene derivative represented by the formula (2) is synthesized from a ketone by one of the following Grignard reactions a, b and c:

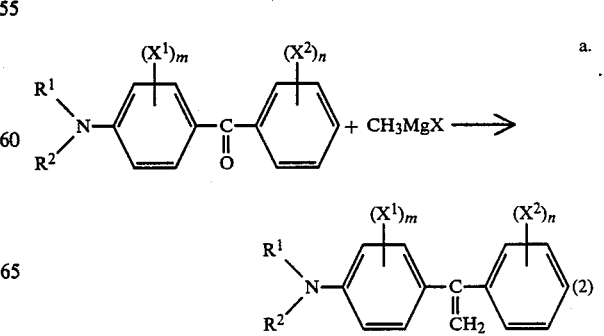

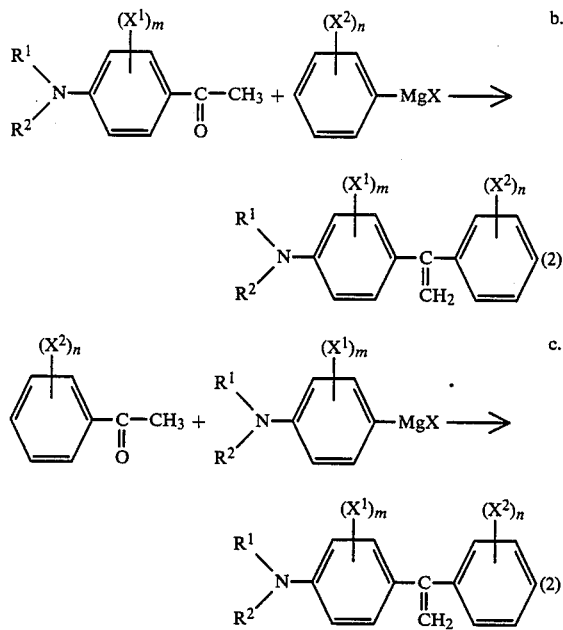

wherein X represents a halogen atom.

Then, 2 mols of an ethylene derivative (2) and 1 mol of a phthalic acid derivative (3) are condensated in the presence of a dehydrating agent such as acetic anhydride, sulfuric acid, etc., and by purifying the reaction product, the divinylphthalide compounds represented by the formula (I) are obtained as nearly colorless crystals.

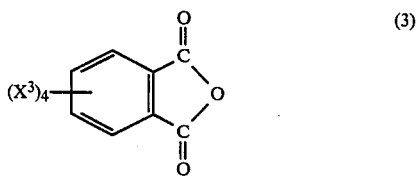

As the concrete examples of the ethylene derivative represented by the formula (2), the following compounds can be exemplified:

1. 1-phenyl-1-(p-dimethylaminophenyl)ethylene
2. 1-(p-methylphenyl)-1-(p-dimethylaminophenyl)ethylene
3. 1-(m,p-dimethylphenyl)-1-(p-dimethylaminophenyl)ethylene
4. 1-(p-methoxyphenyl)-1-(p-dimethylaminophenyl)ethylene
5. 1-(p-ethoxyphenyl)-1-(p-dimethylaminophenyl)ethylene
6. 1-(p-methylphenyl)-1-(p-dimethylamino-o-methylphenyl)-ethylene
7. 1-(p-methylphenyl)-1-(p-dimethylamino-o-ethoxyphenyl)-ethylene
8. 1-(p-methoxyphenyl)-1-(p-dimethylamino-o-methylphenyl)-ethylene
9. 1-phenyl-1-(p-dimethylamino-m-methylphenyl)ethylene
10. 1-(p-methoxy-o-methylphenyl)-1-(p-dimethylaminophenyl)ethylene
11. 1-(p-chlorophenyl)-1-(p-dimethylaminophenyl)ethylene
12. 1-(p-methoxyphenyl)-1-(p-dimethylamino-o-chlorophenyl)-ethylene
13. 1-(p-butoxyphenyl)-1-(p-dimethylaminophenyl)ethylene
14. 1-(p-methoxyphenyl)-1-(p-diethylaminophenyl)ethylene
15. 1-(p-methylphenyl)-1-(p-dipropylamino-o-ethoxyphenyl)-ethylene
16. 1-(p-ethoxyphenyl)-1-(p-dipentylaminophenyl)ethylene
17. 1-phenyl-1-(p-dioctylaminophenyl)ethylene
18. 1-(p-methylphenyl)-1-(p-methylbutylaminophenyl)-ethylene
19. 1-(p-methoxyphenyl)-1-(p-methylcyclohexylaminophenyl)-ethylene
20. 1-(p-methylphenyl)-1-[p-ethyl-(p-methylbenzyl)aminophenyl]ethylene
21. 1-phenyl-1-[p-ethyl-(p-tolyl)aminophenyl]ethylene
22. 1-(p-methoxyphenyl)-1-(p-methylaminophenyl)ethylene
23. 1-(p-methoxyphenyl)-1-(p-methylmethoxyethylaminophenyl)-ethylene
24. 1-(p-chlorophenyl)-1-(p-ethylethoxypropylamino-m-methylphenyl)ethylene
25. 1-(p-methoxyphenyl)-1-(p-diethoxyethylaminophenyl)-ethylene
26. 1-(m,p-dimethylphenyl)-1-(p-propyl-γ-chloropropylaminophenyl)ethylene
27. 1-(p-methoxyphenyl)-1-(p-di-γ-chloropropylaminophenyl)-ethylene
28. 1-(m,p-dimethoxyphenyl)-1-(p-cyclohexyl-γ-chloropropylaminophenyl)ethylene
29. 1-(p-ethoxyphenyl)-1-(p-ethylallylaminophenyl)ethylene
30. 1-(p-isopropoxyphenyl)-1-(p-diallylaminophenyl)ethylene
31. 1-(p-methoxyphenyl)-1-(p-ethylcyclohexylmethylaminophenyl)ethylene
32. 1-(p-methoxyphenyl)-1-(p-dicyclohexylmethylaminophenyl)-ethylene
33. 1-(p-methoxyphenyl)-1-[p-methyl-(3-methylcyclohexy)-aminophenyl]ethylene
34. 1-(p-ethoxy-m-methylphenyl)-1-[p-ethyl-(3,3,5-trimethylcyclohexyl)aminophenyl]ethylene
35. 1-(p-methoxyphenyl)-1-(p-methylfurfurylaminophenyl)-ethylene
36. 1-(p-methoxyphenyl)-1-(p-ethyltetrahydrofurfurylaminophenyl)ethylene
37. 1-(m-methyl-p-ethoxyphenyl)-1-(p-ethyltetrahydropyrane-2-yl-methylaminophenyl)ethylene
38. 1-(p-methoxyphenyl)-1-(p-ditetrahydropyrane-2-ylmethylaminophenyl)ethylene
39. 1-phenyl-1-(p-aminophenyl)ethylene
40. 1-(m,p-dimethoxyphenyl)-1-(p-dimethylaminophenyl)-ethylene
41. 1-(p-bromophenyl)-1-(p-dimethylaminophenyl)ethylene As phthalic acid derivatives represented by the formula (3), for instance, the following compounds can be mentioned:

Tetrachlorophthalic anhydride; 4-chloro-3,5,6-tribromophthalic anhydride; 4,5-dichloro-3,6-dibromophthalic anhydride; 4-bromo-3,5,6-trichlorophthalic anhydride; 4,5-dibromo-3,6-dichlorophthalic anhydride; tetrabromophthalic anhydride; tetrafluorophthalic anhydride; tetraiodophthalic anhydride; 4,5-dichloro-3,6-difluorophthalic anhydride; 4-chloro-3,5,6-triiodophthalic anhydride and 4,5-dichloro-3,6-diiodophthalic anhydride.

In case where a pressure-sensitive recording paper, a heat-sensitive recording paper, etc. is produced with these divinylphthalide compounds, one or more of the compounds, can be used. By mixing not less than two of the compounds, the chromogenic property and the stability in preserving the color image are improved. Moreover, to make the hue and the concentration of developed color, and the stability of color image more complete, various known chromogenic agents which give various hues can be used with the present compound to the extent not to damage the facilities of the present compound.

For instance, the present compound can be used with the chromogenic agent which has the fundamental skeleton such as 3,3-bis(aminophenyl)-6-aminophthalide, 3,3-bis(indolyl)phthalide, 3-aminofluoran, aminobenzofluoran, 2,6-diaminofluoran, 2,6-diamino-3-methylfluoran, spiropyrane, phenothiazine, phenoxazine, leucoauramine, diarylcarbazolylmethane, 3-indolyl-3-(aminophenyl)azaphthalide, triaminofluorenephthalide, tetraaminodivinylphthalide.

When producing a pressure-sensitive recording paper, as a solvent for a chromogenic agent, various solvents of alkylbenzene series, alkylbiphenyl series, alkylnaphthalene series, diarylethane series, hydrogenated terphenyl series and chlorinated paraffin series can be used singly or as a mixture, and for encapsulation, a coacervation method, a interfacial polymerization method or an In-situ method can be applied.

As a developer, clays such as bentonite, activated clay, acid clay, etc.; metal salt of salicyclic acid, salicyclic ester derivatives, salicyclic acid derivatives, etc.; hydroxy compounds such as 2,2-bis(p-hydroxyphenyl)-propane (bisphenol A), esters of p-hydroxybenzoic acid, etc.; p-phenylphenol-formaldehyde resin, p-octylphenolformaldehyde resin and metal salt thereof, are used.

When producing a heat-sensitive recording paper, as a binder, polyvinyl alcohol, methylcellulose, hydroxyethylcellulose, carboxymethylcellulose, gum arabic, gelatine, caseine, starch, polyvinyl pyrrolidone, copolymer of styrene and maleic anhydride, can be used.

As a developer, one or more of the following hydroxy compounds can be used: p-phenylphenol, p-hydroxydiphenyl ether, methyl p-hydroxybenzoate, benzyl p-hydroxybenzoate, 2,2-bis(p-hydroxyphenyl)-propane, 4,4'-thiodiphenol, bis(4-hydroxy-3-methylphenyl)-sulfide, 4,4'-dihydroxydiphenylsulfone, 4-hydroxy-4'-methyldiphenylsulfone, 4-hydroxy-4'-ethyldiphenylsulfone, 3,4-dihydroxy-4'-methyldiphenylsulfone, 4-hydroxy-4'-isopropoxydiphenylsulfone, 4,4'-dihydroxy-3,3'-dimethyldiphenylsulfone, 4,4'-dihydroxy-3,3'-diallyldiphenylsulfone, 1,5-di(4-hydroxyphenylthio)-3-oxapentane, 1,7-di(4-hydroxyphenylthio)-3,5-dioxaheptane, 1,8-di(4-hydroxyphenylthio)-3,6-dioxaoctane, bis(4-hydroxy-3-methylphenyl)sulfide, etc.

As a sensitivity-improving agent, acetoanilide; paraffin wax; carnauba wax; higher fatty acids; esters of a higher fatty acid; amides of a higher fatty acid; phthalic esters; terephthalic esters; benzyl 4-benzyloxybenzoate; naphthol benzyl ether; 1,4-dialkoxynaphthalene; m-terphenyl; p-benzylbiphenyl; dibenzylbenzene; esters of 1-hydroxy-2-naphthoic acid; 1-phenoxy-2-naphthoxy-1-ethane; 1,2-di(3-methylphenoxy)ethane; 1-(2-isopropylphenoxy)-2-naphthoxy-2-ethane; esters of 2-hydroxy-3-naphthoic acid; 4,4'-dialkoxydiphenylsulfone; benzamide; diphenylamine; benzenesulfonamide; benzenesulfonanilide; carbazole; hydroquinone dibenzyl ether; diphenyl carbonate, etc. can be used singly or after mixing together.

Furthermore, in order to improve the light-resistance and the preservability of the color image, it is effective to add an anti-oxidant, an anti-deteriorant or an ultraviolet absorbent, or to overcoat a high polymeric substance.

The present invention will be concretely explained while referring to the Synthetic Examples of the compound represented by the formula (I) and the Production Examples of the chromogenic recording-material with the compound represented by the formula (I) as follow.

SYNTHETIC EXAMPLE 1:

Synthesis of 3,3-bis[2-(p-dimethylaminophenyl)-2-(p-methoxyphenyl)ethenyl]-4,5,6,7-tetrachlorophthalide Into 25 ml of acetic anhydride, 13.0 g of 1-(p-methoxyphenyl)-1-(p-dimethylaminophenyl)ethylene and 9.3 g of tetrachlorophthalic anhydride were added and the mixture was stirred for 2 hours at 120° C. After adding the reaction mixture into 200 ml of water and making the mixture alkaline with sodium hydroxide, the alkaline mixture was extracted with 70 ml of toluene. The solid matter obtained by distilling off toluene from the extract was recrystallized from butanol while purifying with activated carbon to obtain 14.3 g of pale yellow crystals melting at 133°–135° C.

By the elementary analysis, the infrared absorption spectrum and the nuclear magnetic resonance spectrum of the crystals obtained, it was confirmed that the crystals was the object compound represented by the following formula:

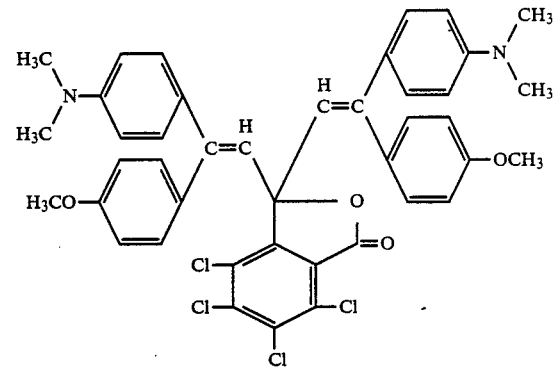

This compound rapidly colored blue-black by activated clay and the λmax in methanol·stannic chloride was 890 nm.

The ethylene derivative, 1-(p-methoxyphenyl)-1-(p-dimethylaminophenyl)ethylene, used in the above reaction, was synthesized as follows.

Into 30 ml of ether, 4 g of metallic magnesium were added and then 0.2 ml of methyl iodide was added to the mixture. After stirring the mixture for a while, a solution prepared by dissolving 24.8 g of methyl iodide into 40 ml of ether was added to the mixture taking 2 hours under a reflux condenser while stirring the mixture.

Separately, a solution was prepared by mixing 18.2 g of 4-methoxy-4'-dimethylaminobenzophenone (melting at 126°–127° C.) and 100 ml of tetrahydrofurane, and the solution was slowly added to the liquid reaction mixture and the whole-matter was stirred for one hour at a temperature of 40° to 50° C. Then the whole matter was mixed with 400 ml of water and 300 ml of toluene and after making the mixture weakly acidic by dilute hydrochloric acid, the acidified mixture was stirred for a whole at 80° C. and separated into an aqueous layer and an organic layer (toluene layer). After adding activated carbon to the toluene layer and filtering the layer while hot, toluene was distilled off from the filtrate to obtain 17.1 g of 1-(p-methoxyphenyl)-1-(p-dimethylaminophenyl)ethylene of pale yellow in color, melting at 123°–125° C.

SYNTHETIC EXAMPLE 2:

Synthesis of 3,3-bis[2-(p-dimethylaminophenyl)-2-(p-ethoxyphenyl)ethenyl]-4,5,6,7-tetrachlorophthalide Into a mixture of 25 ml of acetic anhydride and 75 ml of o-dichlorobenzene, 13.4 g of 1-(p-ethoxyphenyl)-1-(p-dimethylaminophenyl)ethylene (melting at 110°–111° C.) and 21.5 g of tetrachlorophthalic anhydride were added and the mixture was stirred for 6 hours at 120° C. After adding the reaction mixture into 200 ml of water and making the mixture alkaline by sodium hydroxide, the alkaline mixture was extracted with 70 ml of toluene. The solid matter obtained by distilling off toluene from the extract was recrystallized from acetone while purifying with activated carbon to obtain 16.2 g of pale yellow crystals in a yield of 80.8%.

The obtained compound melted at 168°–170° C., and from the elementary analysis, the infrared absorption spectrum and the nuclear magnetic resonance spectrum of this compound, it was confirmed that the substance was the object compound represented by the following formula:

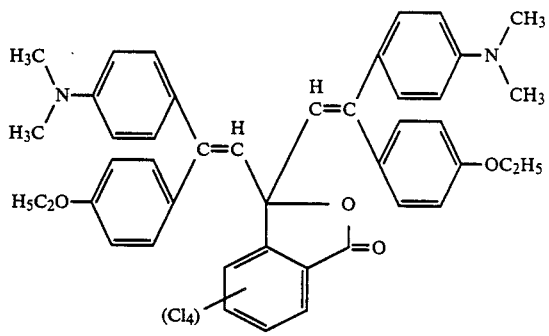

This compound rapidly colored blue-black by activated clay and λmax of this compound in methanol-stannic chloride was 882 nm.

SYNTHETIC EXAMPLES 3–74:

By bringing various ethylene derivatives into reaction with various phthalic acid derivatives in the same manner as in Synthetic Examples 1, 2 and 3, the divinyl compounds shown in Table 1 were synthesized. All the compounds were solid and colorless to pale yellow in color. They were colored rapidly into the hue shown in Table 1.

For preparing a pressure-sensitive recording paper with the divinyl-compound represented by the formula (I), any publicly known method can be used, for instance, the coacervation method disclosed in U.S. Pat. Nos. 2,800,458 and 2,806,457. For preparing the heat-sensitive recording paper, a publicly known method, for instance, the method disclosed in Japanese Patent Publication No. 45-14039/1960, can be used.

TABLE 1

| Compound No. | R¹ | R² | X¹ | X² | X³ | Color | λmax (nm) | M.P. (°C.) |
|---|---|---|---|---|---|---|---|---|
| 3 | C₂H₅— | C₂H₅— | — (m = 0) | p-CH₃O— | Cl | Blue black | 900 | 95 (decomposition) |
| 4 | CH₃— | CH₃— | — (m = 0) | p-n-C₃H₇O— | Cl | Blue black | 888 | 162–164 |
| 5 | CH₃— | CH₃— | — (m = 0) | p-i-C₃H₇O— | Cl | Blue black | 883 | 129–132 |
| 6 | CH₃— | CH₃— | — (m = 0) | p-n-C₄H₉O— | Cl | Blue black | 885 | 180–183 |
| 7 | CH₃— | CH₃— | — (m = 0) | p-i-C₄H₉O— | Cl | Blue black | 885 | 179–182 |
| 8 | CH₃— | C₂H₅— | — (m = 0) | p-CH₃O— | Cl | Blue black | 892 | 120 (decomposition) |
| 9 | CH₃— | C₃H₇— | — (m = 0) | p-CH₃O— | Cl | Blue black | 895 | Difficult to crystallize 215–218 |
| 10 | CH₃— | CH₃— | — (m = 0) | p-CH₃— | Cl | Black | 900 | 115–118 |
| 11 | C₂H₅— | C₃H₇— | — (m = 0) | p-CH₃O— | Cl | Blue Black | 895 | Difficult to crystallize 136–139 |
| 12 | CH₃— | i-C₃H₇— | — (m = 0) | p-CH₃O— | Cl | Blue black | 895 | Difficult to crystallize 105–108 |
| 13 | C₂H₅— | i-C₃H₇— | — (m = 0) | p-CH₃O— | Cl | Blue black | 895 | Difficult to crystallize 125–128 |
| 14 | C₃H₇— | C₃H₇— | — (m = 0) | p-CH₃O— | Cl | Blue black | 897 | 131–135 |
| 15 | CH₃— | C₄H₉— | — (m = 0) | p-CH₃O— | Cl | Blue black | 895 | Difficult to crystallize 133–135 |
| 16 | C₂H₅— | C₄H₉— | — (m = 0) | p-CH₃O— | Cl | Blue black | 892 | 125–128 |
| 17 | C₂H₅— | C₂H₅— | — (m = 0) | p-C₂H₅O— | Cl | Blue black | 895 | 125–128 |
| 18 | CH₃— | CH₃— | — (m = 0) | p-CH₃O—, m-CH₃— | Cl | Blue black | 882 | 131–135 |
| 19 | CH₃— | CH₃— | — (m = 0) | p-n-C₅H₁₁O— | Cl | Blue black | 882 | Difficult to crystallize 133–135 |
| 20 | CH₃— | CH₃— | — (m = 0) | p-CH₃O— | Br | Blue black | 900 | 125–128 |
| 21 | CH₃— | CH₃— | — (m = 0) | p-i-C₅H₁₁O— | Cl | Blue black | 880 | 208–211 |
| 22 | CH₃— | C₂H₅— | — (m = 0) | p-CH₃O—, m-CH₃O— | Cl | Blue black | 890 | 138–141 |
| 23 | CH₃— | C₂H₅— | — (m = 0) | p-C₂H₅O— | Cl | Blue black | 890 | 118–121 |
| 24 | CH₃— | C₃H₇— | — (m = 0) | p-C₂H₅O— | Cl | Blue black | 890 | 185–188 |
| 25 | CH₃— | CH₃— | — (m = 0) | p-C₂H₅— | Cl | Black | 900 | 120–125 |
| 26 | CH₃— | CH₃— | — (n = 0) | — | Cl | Black | 905 | Difficult to crystallize 165–168 |
| 27 | CH₃— | CH₃— | — (m = 0) | p-t-C₄H₉O— | Cl | Blue black | 885 | |
| 28 | CH₃— | CH₃— | — (m = 0) | p-s-C₄H₉O— | Cl | Blue black | 885 | |

TABLE 1-continued

| Compound No. | R¹ | R² | X¹ | X² | X³ | Color | λmax (nm) | M.P. (°C.) |
|---|---|---|---|---|---|---|---|---|
| 29 | $CH_3-$ |  | — (m = 0) | p-CH$_3$O— | Cl | Blue black | 890 | 165 (decomposition) |
| 30 | $CH_3-$ | $CH_3-$ | — (m = 0) | p-CH$_3$O— | 5,6-Cl$_2$—, 4,7-Br$_2$— | Blue black | 884 | 145–148 |
| 31 | $CH_3-$ | $CH_3-$ | — (m = 0) | p-Cl— | Cl | Black | 915 | 133–135 |
| 32 | $CH_3-$ | $CH_3-$ | — (m = 0) | m-CH$_3$—, p-CH$_3$— | Cl | Black | 900 | 150–155 |
| 33 | $C_2H_5-$ | $C_2H_5-$ | O—CH$_3$ | p-CH$_3$— | Cl | Black | 900 | Difficult to crystallize |
| 34 | $C_2H_5-$ | $C_2H_5-$ | O—C$_3$H$_7$O— | p-CH$_3$O— | Cl | Violetish black | 820 | Difficult to crystallize |
| 35 | $C_4H_9-$ | $C_4H_9-$ | — (m = 0) | p-CH$_3$— | Cl | Black | 910 | 135–138 |
| 36 | $C_2H_5-$ | $C_5H_{11}-$ | — (m = 0) | p-CH$_3$O— | Cl | Blue black | 890 | Difficult to crystallize |
| 37 | $C_6H_{13}-$ | $C_6H_{13}-$ | — (m = 0) | p-CH$_3$— | Cl | Black | 910 | Difficult to crystallize |
| 38 | $C_2H_5-$ | 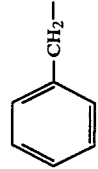 | — (n = 0) | — (n = 0) | Cl | Black | 920 | Difficult to crystallize |
| 39 | $C_2H_5-$ | 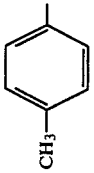 | — (m = 0) | p-CH$_3$— | Cl | Black | 910 | Difficult to crystallize |
| 40 | $CH_3-$ | $CH_3-$ | — (m = 0) | p-CH$_3$O— | 5-Cl—, (Br)$_3$— | Blue black | 885 | 130–135 |
| 41 | $CH_3-$ | $CH_3-$ | — (m = 0) | p-C$_4$H$_9$O— | 5,6-(Cl)$_2$—, 4,7-(Br)$_2$— | Blue black | 882 | 178–181 |
| 42 | $CH_3-$ | $CH_3-$ | — (m = 0) | p-C$_6$H$_{13}$O— | Br | Blue black | 882 | Difficult to crystallize |
| 43 | $CH_3-$ | $CH_3-$ | — (m = 0) | — | Br | Black | 910 | 145–148 |
| 44 | $CH_3-$ | $CH_3-$ | — (m = 0) | — (n = 0) | Br | Black | 890 | 224–226 |
| 45 | $CH_3-$ | $CH_3-$ | — (m = 0) | p-CH$_3$— | 5-Cl—, (Br)$_3$— | Black | 900 | 218–222 |
| 46 | $CH_3-$ | $CH_3-$ | — (m = 0) | p-t-C$_4$H$_9$— | Cl | Black | 895 | 198–200 |
| 47 | $CH_3-$ | $CH_3-$ | — (m = 0) | m-CH$_3$O—, p-CH$_3$O— | Br | Blue Black | 890 | 136–140 |

TABLE 1-continued

| Compound No. | R¹ | R² | X¹ | X² | X³ | Color | λmax (nm) | M.P. (°C) |
|---|---|---|---|---|---|---|---|---|
| 48 | $C_2H_5-$ | $C_2H_5-$ | — (m = 0) | p-$CH_3O-$ | Br | Blue black | 903 | Difficult to crystallize |
| 49 | $C_2H_5-$ | $C_2H_5-$ | m-$CH_3-$ (m = 0) | p-$CH_3-$ | Br | Black | 905 | 131–135 |
| 50 | $C_2H_5-$ | $C_2H_5-$ | m-$CH_3-$ | p-$CH_3O-$ | Br | Blue black | 910 | Difficult to crystallize |
| 51 | $C_4H_9-$ | $C_4H_9-$ | — (m = 0) | p-$C_2H_5O-$ | Br | Blue black | 900 | Difficult to crystallize |
| 52 | $C_2H_5-$ | i-$C_5H_{11}-$ | — (m = 0) | p-t-$C_4H_9-$ | Br | Black | 905 | Difficult to crystallize |
| 53 | $C_2H_5-$ |  | — (m = 0) | p-$CH_3O-$ | Br | Blue black | 900 | 165–168 |
| 54 | $CH_3-$ |  | — (m = 0) | p-$CH_3O-$ | Br | Blue black | 910 | 185–188 |
| 55 | $C_2H_5-$ |  | m-$CH_3O-$ | m-$(CH_3)-$, p-$(CH_3)-$ | 5-Cl—, (Br)₃— | Black | 900 | Difficult to crystallize |
| 56 | $CH_3-$ | $CH_3OC_2H_4-$ | — (m = 0) | p-$CH_3O-$ | Cl | Blue black | 885 | 95 (decomposition) |
| 57 | $CH_3-$ | $CH_2=CH-CH_2-$ | — (m = 0) | p-$CH_3-$ | Cl | Reddish black | 900 | 113–115 |
| 58 | $C_2H_5-$ | $CH_3OC_3H_6-$ | — (m = 0) | p-$CH_3O-$ | Br | Blue black | 880 | Difficult to crystallize |
| 59 | $CH_3-$ | $C_2H_5OC_3H_6-$ | — | p-$CH_3O-$, m-$CH_3O-$ | Cl | Blue black | 887 | 112–115 |
| 60 | $CH_3OC_2H_4-$ | $CH_3OC_2H_4-$ | — | p-Cl— | Cl | Reddish black | 920 | Difficult to crystallize |
| 61 | $CH_3-$ | $CH_3OC_3H_6-$ | (m = 0) O—$CH_3$ | p-$CH_3O-$ | Cl | Blue black | 880 | Difficult to crystallize |
| 62 | $CH_3-$ |  | — (m = 0) | p-$C_2H_5O-$, m-$CH_3-$ | Cl | Blue black | 890 | 125–129 |
| 63 | $C_2H_5-$ |  | — (m = 0) | p-t-$C_4H_9-$ | Cl | Black | 897 | Difficult to crystallize |

TABLE 1-continued

| Compound No. | $R^1$ | $R^2$ | $X^1$ | $X^2$ | $X^3$ | Color | $\lambda$max (nm) | M.P. (°C.) |
|---|---|---|---|---|---|---|---|---|
| 64 | $CH_3-$ | $CH_2=CH-CH_2-$ | — ($m=0$) | p-$CH_3-$ | Br | Reddish black | 892 | 116-120 |
| 65 | $CH_3$ | $CH_2=CH-CH_2-$ | — ($m=0$) | p-$CH_3-$ | 5-Cl, (Br)$_3-$ | Reddish black | 893 | 108-112 |
| 66 | $CH_3-$ | $CH_2=CH-CH_2-$ | — ($m=0$) | p-$CH_3-$ | 5,6-Cl$_2-$, 4,7-Br$_2-$ | Reddish black | 895 | 105-108 |
| 67 | $CH_3-$ | $CH_2=CH-CH_2-$ | — ($m=0$) | p-$CH_3-$ | F | Reddish black | 891 | Difficult to crystallize |
| 68 | H— | $CH_3-$ | — ($m=0$) | p-$CH_3O-$ | Cl | Blue black | 870 | Difficult to crystallize |
| 69 | $CH_3-$ | $CH_3-$ | — ($m=0$) | p-($CH_3O$)— phenyl —O— | Cl | Blue black | 892 | 83 (decomposition) |
| 70 | $CH_3-$ | $CH_3-$ | — ($m=0$) | p-$CH_3OC_2H_4O-$ | Cl | Blue black | 890 | 145-148 |
| 71 | $CH_3-$ | $CH_3-$ | — ($m=0$) | p-(cyclohexyl-O—) | Cl | Blue black | 895 | 151-154 |
| 72 | $CH_3-$ | $CH_3-$ | — ($m=0$) | p-(phenyl-$CH_2-$O—) | Cl | Blue black | 897 | 168-171 |
| 73 | $CH_3-$ | $CH_3-$ | — ($m=0$) | p-($CH_3O$—phenyl—O—) | Br | Blue black | 895 | Difficult to crystallize |
| 74 | $CH_3-$ | $CH_3-$ | — ($m=0$) | p-($C_8H_{17}O$—) | Cl | Blue black | 893 | Difficult to crystallize |

PRODUCTION EXAMPLE 1:

Production of a pressure-sensitive copying paper.

Into 95 parts by weight of monoisopropylbiphenyl, 5 parts by weight of the compound of Example 2, namely, 3,3-bis[2-(p-dimethylaminophenyl)-2-(p-ethoxyphenyl)-ethenyl]-4,5,6,7-tetrachlorophthalide, were dissolved and a solution of 24 parts by weight of gelatine and 24 parts by weight of gum arabic into 400 parts by weight of water, of which pH was adjusted to 7, was added to the monoisopropylbiphenyl solution and the mixture was emulsified by a homogenizer. Into the emulsion, 100 parts by weight of warm water were added and after stirring the mixture for 30 minutes at 50° C. about one part by weight of an aqueous 10% solution of sodium hydroxide was added and the mixture was further stirred for another 30 minutes at the same temperature.

In the next step, dilute acetic acid was added to the mixture to adjust the pH to 4.5 and after stirring for about one hour at 50° C., the mixture was cooled to 0° to 5° C. and stirred for 30 minutes. Then, 35 parts by weight of an aqueous 4% solution of glutaraldehyde were slowly added to the mixture to harden the resulting capsules and pH of the mixture was adjusted to 6 by adding a dilute aqueous solution of sodium hydroxide to complete the capsulation. During the operations, no coloring was observed.

The capsule suspension obtained was uniformly coated on a sheet of paper by a wire-bar so that the coated weight of capsules after drying became 6 g/m² and the sheet was dried to obtain a capsule-coated paper sheet (the upper paper sheet).

On piling the upper paper sheet onto a sheet of paper coated with a phenol-formaldehyde resin as a developer and applying writing pressure by a ball-pen on the sheets of paper, letters of deep black in color rapidly appeared on the piled-up sheets of paper.

The color image appeared were excellent in light-resistance and moisture-resistance and since the image had a strong absorption in the range of 800 to 1000 nm, it was possible to read the letters by OCR. Furthermore, the surface of the paper coated with the capsules had an excellent light-resistance, and its color and chromogenic ability were not reduced by sun light.

COMPARATIVE EXAMPLE 1:

In the same manner as in Production Example 1 except for using 5 parts by weight of the compound (D) as the chromogenic agent, a pressure-sensitive copying paper was prepared.

On subjecting the pressure-sensitive copying paper to color-development by a lower paper sheet on which a phenolformaldehyde resin had been applied, a light green image appeared slowly.

As the absorption of near infrared rays by the image was weak, it was difficult to read it by OCR (refer to FIG. 1).

PRODUCTION EXAMPLE 2:

Production of a heat-sensitive recording paper:
(1) Preparation of a liquid dispersion of a chromogenic agent (A-liquid).

A mixture of the following recipe was pulverized by a paintshaker (made by Toyo-Seiki Co., Ltd.) until the mean diameter of the particles of the chromogenic agent bacame 2 μm:

5 parts by weight of 3,3-bis[2-(1-p-dimethylaminophenyl)-2-(p-methoxyphenyl)ethenyl]-4,5,6,7-tetrachlorophthalide (Synthetic Example 1)
15 parts by weight of kaoline,
100 parts by weight of an aqueous 10% solution of polyvinyl alcohol and
85 parts by weight of water (2) Preparation of a liquid dispersion of a developer and a sensitizer (B-liquid).

A mixture of the following recipe was pulverized by a paintshaker until the mean diameter of the particles of developer and sensitizer became 3 μm:

15 parts by weight of bisphenol A,
10 parts by weight of zinc stearate,
15 parts by weight of stearic amide and
150 parts by weight of an aqueous 10% solution of polyvinyl alcohol.

(3) Preparation and application of a liquid heat-sensitive material.

By mixing 10 parts by weight of A-liquid and 6.5 parts by weight of B-liquid, a liquid heat-sensitive material was obtained. The liquid material was coated on a sheet of paper by a wire-bar uniformly so that the coated weight of solid materials after drying became 6 g/m² and the sheet of paper was dried to obtain a heat-sensitive recording paper.

The heat-sensitive recording paper was nearly colorless and did not show any spontaneous coloring (refer to FIG. 3). The heat-sensitive recording paper showed a dark-black color by the heating with a heated pen. The color image obtained was excellent in light-resistance and moisture-resistance and as the color image had a strong absorption in the range of 700 and 1050 nm, it was possible to read the image by OCR.

The same results have been obtained on using the compounds in another Synthetic Examples.

COMPARATIVE EXAMPLE 2:

In the same manner as in Production Example 2 except for using 5 parts by weight of the compound (A), a heat-sensitive recording paper was obtained. Although the heat-sensitive recording paper was colored into black by heating with a heated pen, as the color image did not absorb any near infrared rays, it was impossible to read the color image by OCR (refer to FIG. 2).

COMPARATIVE EXAMPLE 3:

In the same manner as in Production Example 2 except for using 5 parts by weight of the compound (B), a heat-sensitive recording paper was obtained. The heat-sensitive recording paper showed yellowish green spontaneous coloring. On heating the paper with a heated pen, green color was developed (refer to FIGS. 2 and 3).

From the above Production Examples and Comparative Examples, it has been confirmed that the divinyl compound according to the present invention is the excellent chromogenic agent for the recording materials.

What is claimed is:
1. A divinyl compound represented by the formula (I):

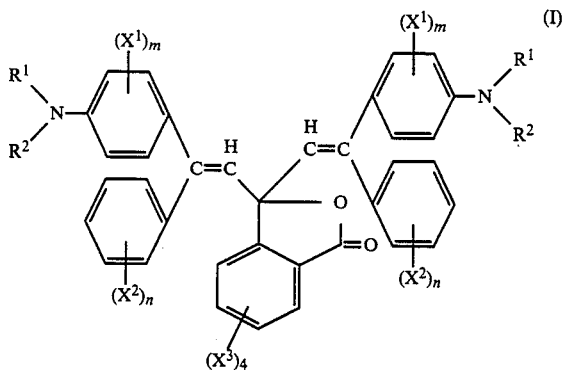

wherein $X^1$ represents an alkyl group, an alkoxy group or a halogen atom; $X^2$ represents an alkyl group, an alkoxy group, a halogen atom or $R^3O$—; $X^3$ represents a halogen atom; $R^1$ represents a hydrogen atom, an alkyl group, an alkoxyalkyl group, a haloalkyl group, an alkenyl group, an aralkyl group, a cyclohexylmethyl group, a methylcyclohexyl group, a trimethylcyclohexyl group, a furfuryl group, a tetrahydrofurfuryl group or a tetrahydropyran-2-yl-methyl group; $R^2$ represents a cycloalkyl group, a phenyl group, a benzyl group, a phenyl or a benzyl group substituted by a chlorine atom, a bromine atom or an alkyl or alkoxy group both of which have not more than four carbon atoms or any one of $R^1$; $R^3$ represents an aryl group, a cycloalkyl group, an alkoxyalkyl group, an alkenyl group, a haloalkyl group or an aralkyl group and m and n respectively represent an integer of 0, 1, 2 or 3, wherein $X^1$ of $(X^1)_m$ or $X^2$ of $(X^2)_n$ can be same or different when m, n or both are not less than 2 and $X^3$ of $(X^3)_4$ can be same or different.

2. A divinyl compound according to claim 1, wherein $R^1$ represents an alkyl group of not more than six carbon atoms, an alkoxyalkyl group of not more than six carbon atoms, a haloalkyl group of not more than six carbon atoms, an alkenyl group of not more than six carbon atoms, a cyclohexyl group, a cyclohexylmethyl group, a methylcyclohexyl group, a trimethylcyclohexyl group, a furfuryl group, a tetrahydrofurfuryl group, a tetrahydropyrane-2-yl-methyl group, a benzyl group or a benzyl group substituted with an alkyl group of not more than four carbon atoms; $R^2$ represents a phenyl group, a phenyl group substituted with a chlorine atom or an alkyl group of not more than four carbon atoms or any one of $R^1$; $X^1$ represents a methyl group, a methoxy group or an ethoxy group; $X^2$ represents a halogen atom, an alkyl group of not more than six carbon atoms, an alkoxy group of not more than six carbon atoms, an alkoxyalkoxy group of not more than six carbon atoms, a cyclohexyloxy group, a benzyloxy group, a phenoxy group or a phenoxy or a benzyloxy group substituted with an alkyl or an alkoxy group both of which have not more than four carbon atoms; m is 0 or 1 and n is 0, 1 or 2.

3. A divinyl compound according to claim 2, wherein $R^1$ represents an alkyl group of not more than six carbon atoms; $R^2$ represents an alkyl group of not more than six carbon atoms or a cyclohexyl group; $X^2$ represents a halogen atom, an alkyl group of not more than six carbon atoms, an alkoxy group of not more than six carbon atoms, and alkoxyalkoxy group of not more than six carbon atoms, a cyclohexyloxy group, a phenoxy group, a benzyloxy group or a phenoxy or benzyloxy group substituted with an alkyl or an alkoxy group both of which have not more than four carbon atoms; $X^3$ represents a chloride atom, m is 0 and n is 0, 1 or 2.

4. A divinyl compound according to claim 3, wherein $R^1$ represents a methyl group or an ethyl group; $R^2$ represents a methyl group, an ethyl group, an n-propyl group or an iso-propyl group; $X^2$ represents a methyl group, an alkoxy group of not more than five carbon atoms and n is 1 or 2.

5. A divinyl compound according to claim 1, wherein said divinyl compound is 3,3-bis[2-(p-dimethylaminophenyl)-2-(p-methoxyphenyl)ethenyl]-4,5,6,7-tetrachlorophthalide.

6. A divinyl compound according to claim 1, wherein said divinyl compound is 3,3-bis[2-(p-dimethylaminophenyl)-2-(p-ethoxyphenyl)ethenyl]-4,5,6,7-tetrachlorophthalide.

7. A divinyl compound according to claim 1, wherein said divinyl compound is 3,3-bis[2-(p-diethylaminophenyl)-2-(methoxyphenyl)ethenyl]-4,5,6,7-tetrachlorophthalide.

8. A divinyl compound according to claim 1, wherein said divinyl compound is 3,3-bis[2-(p-dimethylaminophenyl)-2-(p-propoxyphenyl)ethenyl]-4,5,6,7-tetrachlorophthalide.

9. A divinyl compound according to claim 1, wherein said divinyl compound is 3,3-bis[2-(p-dimethylaminophenyl)-2-(p-iso-propoxyphenyl)ethenyl]-4,5,6,7-tetrachlorophthalide.

10. A divinyl compound according to claim 1, wherein said divinyl compound is 3,3-bis[2-(p-dimethylaminophenyl)-2-(p-butoxyphenyl)ethenyl]-4,5,6,7-tetrachlorophthalide.

11. A divinyl compound according to claim 1, wherein said divinyl compound is 3,3-bis[2-(p-dimethylaminophenyl)-2-(p-iso-butoxyphenyl)ethenyl]-4,5,6,7-tetrachlorophthalide.

12. A divinyl compound according to claim 1, wherein said divinyl compound is 3,3-bis[2-(p-methylethylaminophenyl)-2-(p-methoxyphenyl)ethenyl]-4,5,6,7-tetrachlorophthalide.

13. A divinyl compound according to claim 1, wherein said divinyl compound is 3,3-bis[2-(p-methylpropylaminophenyl)-2-(p-methoxyphenyl)ethenyl]-4,5,6,7-tetrachlorophthalide.

14. A divinyl compound according to claim 1, wherein said divinyl compound is 3,3-bis[2-(p-dimethylaminophenyl)-2-(p-methylphenyl)ethenyl]-4,5,6,7-tetrachlorophthalide.

15. A divinyl compound according to claim 1, wherein said divinyl compound is 3,3-bis[2-(p-ethylpropylaminophenyl)-2-(p-methoxyphenyl)ethenyl]-4,5,6,7-tetrachlorophthalide.

16. A divinyl compound according to claim 1, wherein said divinyl compound is 3,3-bis[2-(p-methyl-iso-propylaminophenyl)-2-(p-methoxyphenyl)ethenyl]-4,5,6,7-tetrachlorophthalide.

17. A divinyl compound according to claim 1, wherein said divinyl compound is 3,3-bis[2-(p-ethyl-iso-propylaminophenyl)-2-(p-methoxyphenyl)ethenyl]-4,5,6,7-tetrachlorophthalide.

18. A divinyl compound according to claim 1, wherein said divinyl compound is 3,3-bis[2-(p-dipropylaminophenyl)-2-(p-methoxyphenyl)ethenyl]-4,5,6,7-tetrachlorophthalide.

19. A divinyl compound according to claim 1, wherein said divinyl compound is 3,3-bis[2-(p-methylbutylaminophenyl)-2-(p-methoxyphenyl)ethenyl]-4,5,6,7-tetrachlorophthalide.

20. A divinyl compound according to claim 1, wherein said divinyl compound is 3,3-bis[2-(p-ethylbutylaminophenyl)-2-(p-methoxyphenyl)ethenyl]-4,5,6,7-tetrachlorophthalide.

21. A divinyl compound according to claim 1, wherein said divinyl compound is 3,3-bis[2-(p-diethylaminophenyl)-2-(p-ethoxyphenyl)ethenyl]-4,5,6,7-tetrachlorophthalide.

22. A divinyl compound according to claim 1, wherein said divinyl compound is 3,3-bis[2-(p-dimethylaminophenyl)-2-(m-methyl-p-methoxyphenyl)ethenyl]-4,5,6,7-tetrachlorophthalide.

23. A divinyl compound according to claim 1, wherein said divinyl compound is 3,3-bis[2-(p-dimethylaminophenyl)-2-(p-pentyloxyphenyl)ethenyl]-4,5,6,7-tetrachlorophthalide.

24. A divinyl compound according to claim 1, wherein said divinyl compound is 3,3-bis[2-(p-dimethylaminophenyl)-2-(p-methoxyphenyl)ethenyl]-4,5,6,7-tetrabromophthalide.

25. A divinyl compound according to claim 1, wherein said divinyl compound is 3,3-bis[2-(p-dimethylaminophenyl)-2-(p-iso-pentyloxyphenyl)ethenyl]-4,5,6,7-tetrachlorophthalide.

26. A divinyl compound according to claim 1, wherein said divinyl compound is 3,3-bis[2-(p-dimethylaminophenyl)-2-(m,p-dimethoxyphenyl)ethenyl]-4,5,6,7-tetrachlorophthalide.

27. A divinyl compound according to claim 1, wherein said divinyl compound is 3,3-bis[2-(p-methylethylaminophenyl)-2-(p-ethoxyphenyl)ethenyl]-4,5,6,7-tetrachlorophthalide.

28. A divinyl compound according to claim 1, wherein said divinyl compound is 3,3-bis[2-(p-methylpropylaminophenyl)-2-(p-ethoxyphenyl)ethenyl]-4,5,6,7-tetrachlorophthalide.

29. A divinyl compound according to claim 1, wherein said divinyl compound is 3,3-bis[2-(p-dimethylaminophenyl)-2-(p-ethylphenyl)ethenyl]-4,5,6,7-tetrachlorophthalide.

30. A divinyl compound according to claim 1, wherein said divinyl compound is 3,3-bis[2-(p-dimethylaminophenyl)-2-phenylethenyl]-4,5,6,7-tetrachlorophthalide.

31. A divinyl compound according to claim 1, wherein said divinyl compound is 3,3-bis[2-(p-dimethylaminophenyl)-2-(p-tert-butoxyphenyl)ethenyl]-4,5,6,7-tetrachlorophthalide.

32. A divinyl compound according to claim 1, wherein said divinyl compound is 3,3-bis[2-(p-dimethylaminophenyl)-2-(p-sec-butoxyphenyl)ethenyl]-4,5,6,7-tetrachlorophthalide.

33. A divinyl compound according to claim 1, wherein said divinyl compound is 3,3-bis[2-(p-methylcyclohexylaminophenyl)-2-(p-methoxyphenyl)ethenyl]-4,5,6,7-tetrachlorophthalide.

34. A divinyl compound according to claim 1, wherein said divinyl compound is 3,3-bis[2-(p-dimethylaminophenyl)-2-(p-methoxyphenyl)ethenyl]-5,6-dichloro-4,7-dibromophthalide.

35. A divinyl compound according to claim 1, wherein said divinyl compound is 3,3-bis[2-(p-methylmethoxyethylaminophenyl)-2-(p-methoxyphenyl)ethenyl]-4,5,6,7-tetrachlorophthalide.

36. A divinyl compound according to claim 1, wherein said divinyl compound is 3,3-bis[2-(p-methylallylaminophenyl)-2-(p-methylphenyl)ethenyl]-4,5,6,7-tetrachlorophthalide.

37. A divinyl compound according to claim 1, wherein said divinyl compound is 3,3-bis{2-(p-dimethylaminophenyl)-2-[p-methoxyphenoxy)phenyl]ethenyl}-4,5,6,7-tetrachlorophthalide.

* * * * *